United States Patent
Fabian Galvez et al.

(10) Patent No.: US 12,159,692 B2
(45) Date of Patent: Dec. 3, 2024

(54) METHOD AND SYSTEM FOR POLYPROPYLENE AND POLYPROPYLENE ARTICLE PRODUCTION MODELING USING ARTIFICIAL INTELLIGENCE ALGORITHMS

(71) Applicant: Braskem S.A., Camaçari (BR)

(72) Inventors: Rodrigo Fabian Galvez, São Paulo (BR); Gilson Pereira Fontes Junior, São Paulo (BR); Francisco Carlos Ruiz, São Paulo (BR); Ricardo Luis Santos Brasil, São Paulo (BR)

(73) Assignee: Braskem S.A., Camaçari (BR)

( * ) Notice: Subject to any disclaimer, the term of this patent is extended or adjusted under 35 U.S.C. 154(b) by 822 days.

(21) Appl. No.: 17/071,774

(22) Filed: Oct. 15, 2020

(65) Prior Publication Data

US 2021/0110891 A1 Apr. 15, 2021

Related U.S. Application Data

(60) Provisional application No. 62/915,326, filed on Oct. 15, 2019.

(51) Int. Cl.
| | | |
|---|---|---|
| *G16C 20/70* | (2019.01) | |
| *G06N 3/08* | (2023.01) | |
| *G06N 5/01* | (2023.01) | |
| *G16C 60/00* | (2019.01) | |

(52) U.S. Cl.
CPC ............ *G16C 20/70* (2019.02); *G06N 3/08* (2013.01); *G06N 5/01* (2023.01); *G16C 60/00* (2019.02)

(58) Field of Classification Search
CPC .......... G16C 20/70; G16C 60/00; G06N 3/08; G06N 5/01; G06Q 10/0633
See application file for complete search history.

(56) References Cited

U.S. PATENT DOCUMENTS

| 10,061,300 B1 | 8/2018 | Coffman et al. |
|---|---|---|
| 2016/0148850 A1 | 5/2016 | David |

FOREIGN PATENT DOCUMENTS

| CN | 109507888 A | * 3/2019 | ........... G05B 13/042 |
|---|---|---|---|
| WO | 2001004166 A1 | 1/2001 | |

OTHER PUBLICATIONS

Mannodi-Kanakkithodi, A. Scoping the polymer genome: a roadmap for rational polymer dielectrics design and beyond. Materials Today 21(7): 785-796. (Year: 2018).*
Maddah, HA. Polypropylene as a promising plastic: a review. American Journal of Polymer Science 6(1): 1-11. (Year: 2016).*
Richards JR. Measurement and control of polymerization reactors. Computers and Chemical Engineering 30: 1447-1463. (Year: 2006).*
B. Farsang et al.; "PCA Based Data Reconciliation in Soft Sensor Development—Application for Melt Flow Index Estimation", Chemical Engineering Transactions, vol. 43, 2015, pp. 1555-1560 (6 pages).
"PP—Polypropylene", CPMAI—Chemicals & Petrochemicals Manufacturers' Association, India, Sep. 2019 <http://cpmaindia.com/pp.php> (3 pages).
S. Altarazi et al.; "Machine Learning Models for Predicting and Classifying the Tensile Strength of Polymeric Films Fabricated via Different Production Processes", Materials, vol. 12, No. 9, May 7, 2019 (14 pages).
V. Prasad et al.; "Product property and production rate control of styrene polymerization", Journal of Process Control, vol. 12, No. 3, 2002, pp. 353-372 (20 pages).
International Search Report issued in corresponding International Application No. PCT/IB2020/020064, mailed Jan. 11, 2021 (6 pages).
Written Opinion issued in corresponding International Application No. PCT/IB2020/020064, mailed Jan. 11, 2021 (10 pages).

* cited by examiner

*Primary Examiner* — Soren Harward
*Assistant Examiner* — Robert J Kallal
(74) *Attorney, Agent, or Firm* — Osha Bergman Watanabe & Burton LLP

(57) ABSTRACT

A method may include obtaining, by a computer processor, first data from a first entity regarding a polymerization process. The method may further include obtaining, by the computer processor, second data from a second entity regarding a production process. The method may further include generating, by the computer processor, a decision tree model using the first data, the second data, and an artificial intelligence algorithm.

16 Claims, 8 Drawing Sheets

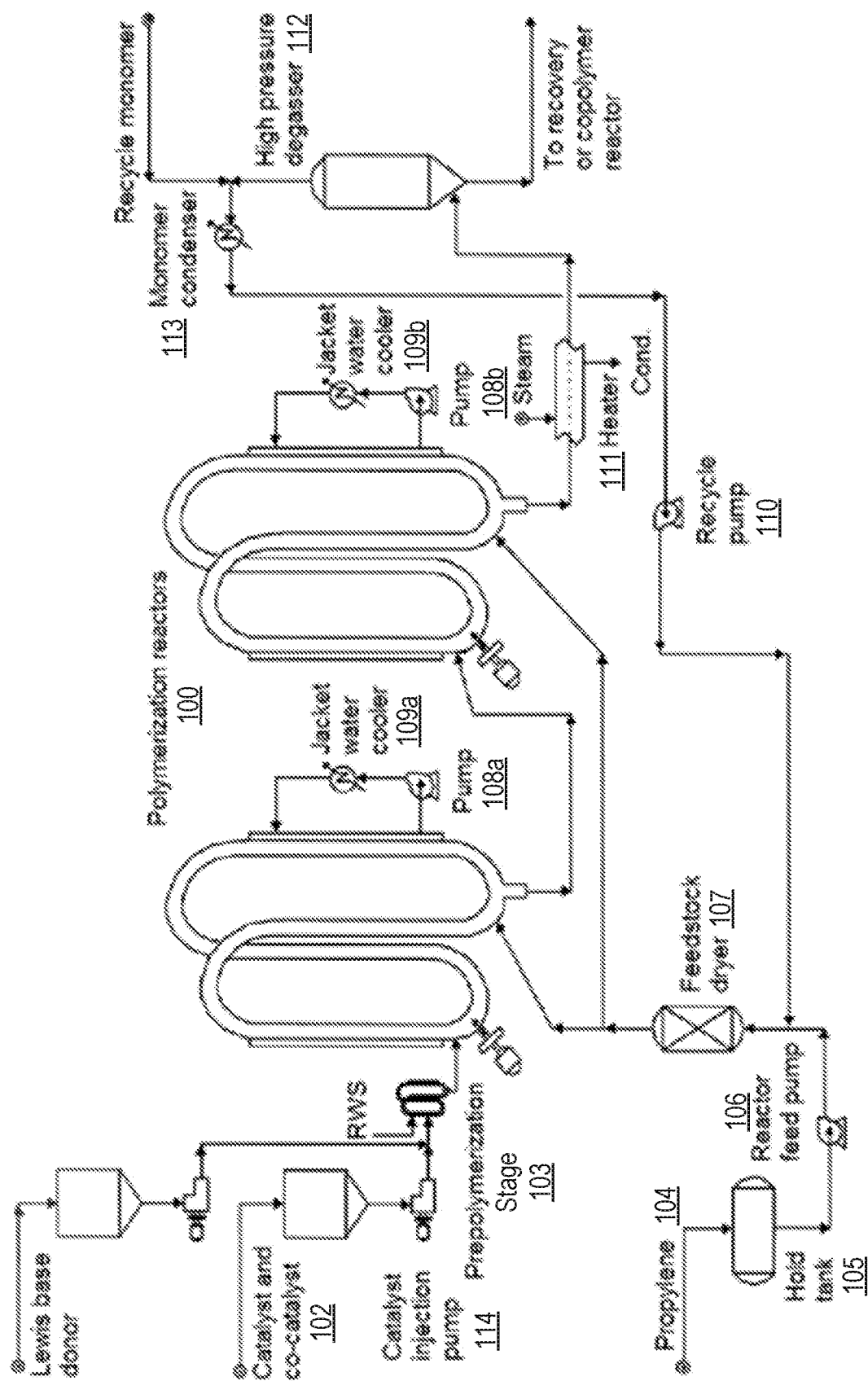
FIG. 1.1

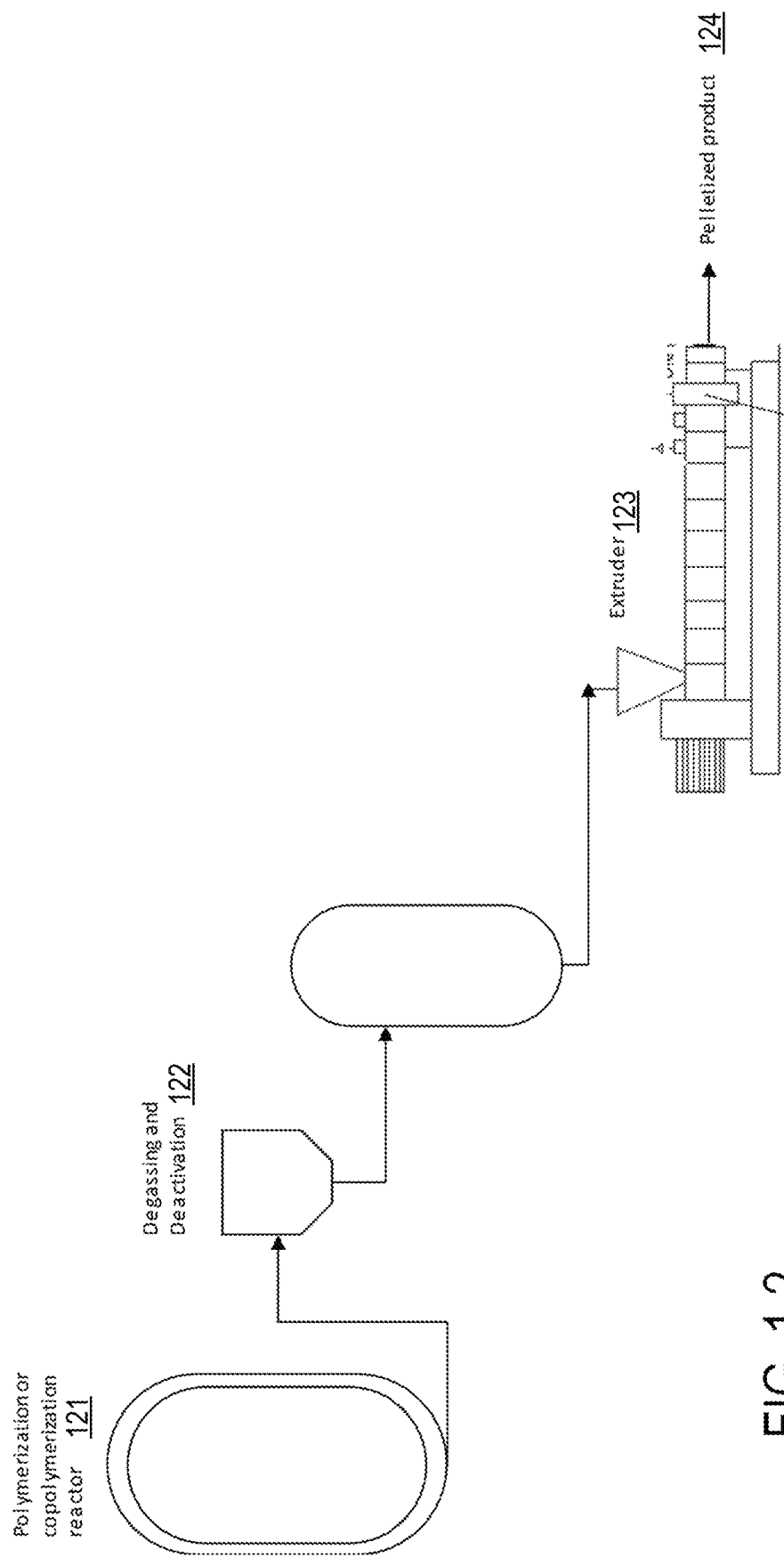
FIG. 1.2

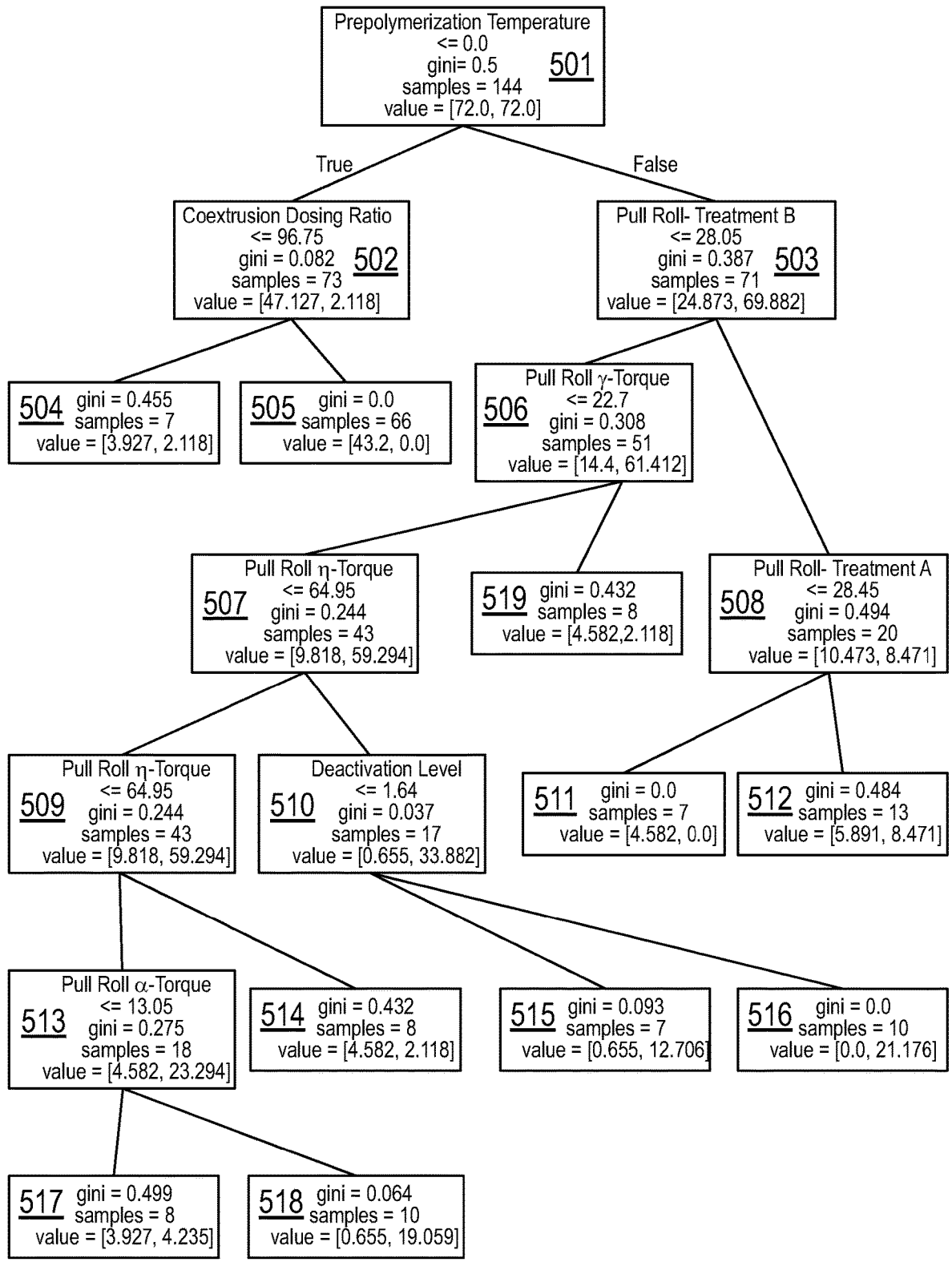
FIG. 5.1

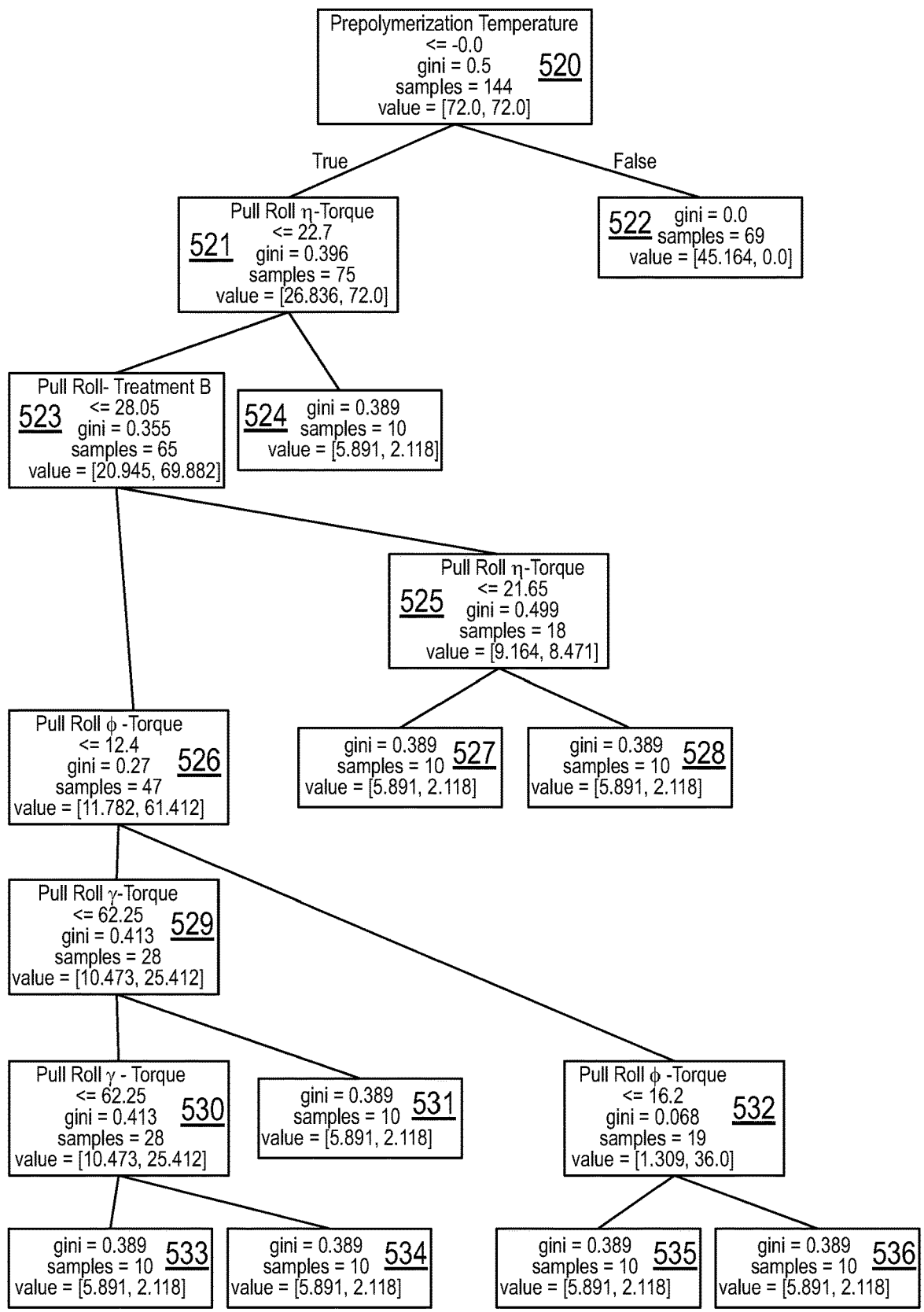
FIG. 5.2

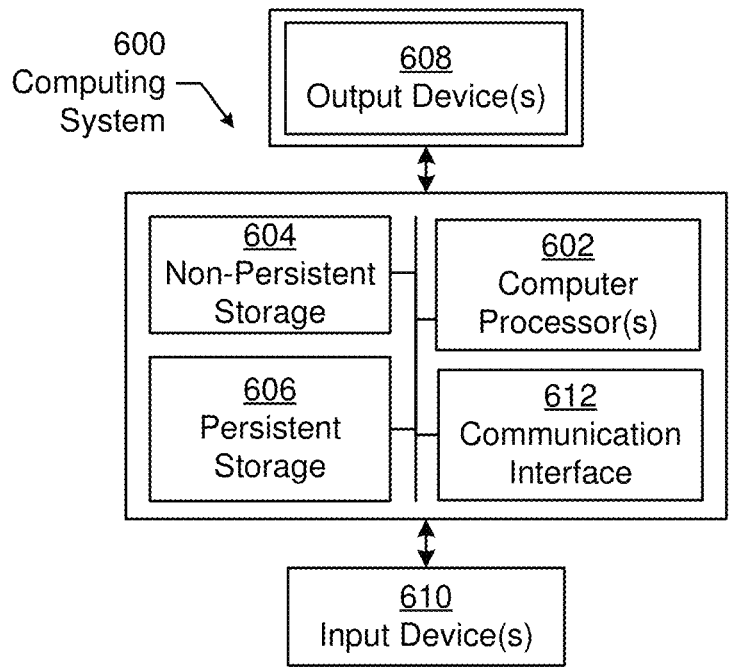
*FIG. 6.1*
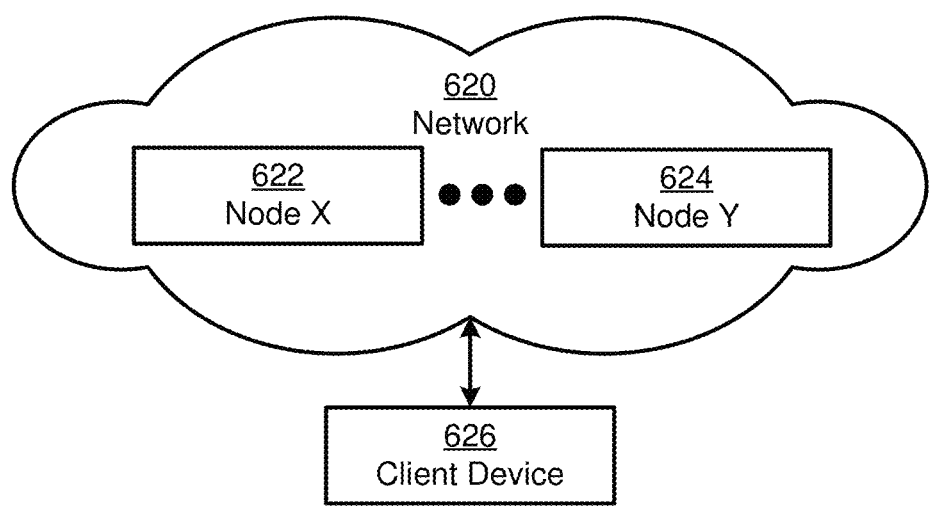
*FIG. 6.2*

METHOD AND SYSTEM FOR POLYPROPYLENE AND POLYPROPYLENE ARTICLE PRODUCTION MODELING USING ARTIFICIAL INTELLIGENCE ALGORITHMS

CROSS-REFERENCE TO RELATED APPLICATIONS

This application claims priority to U.S. Provisional Patent Application Ser. No. 62/915,326, which was filed on Oct. 15, 2019, and is incorporated herein by reference.

BACKGROUND

The manufacture of polyolefin materials such as polyethylene (PE) and polypropylene (PP) are the highest production volume of a synthetic polymer ever invented. The success of these materials were greatly achieved due to its low production cost, energy efficiency, low greenhouse gas emission, versatility to produce a wide range of polymers with different properties, and high polymer processability. The wide range of articles produced with polyolefin materials includes films, molded products, foams, pipes, textiles, and the like.

BRIEF DESCRIPTION OF DRAWINGS

FIGS. 1.1 and 1.2 show systems in accordance with one or more embodiments of the technology.

FIGS. 3, 4, 5.1, and 5.2 show examples in accordance with one or more embodiments of the technology.

FIGS. 6.1 and 6.2 show a computing system in accordance with one or more embodiments of the technology.

SUMMARY

Figure 2:
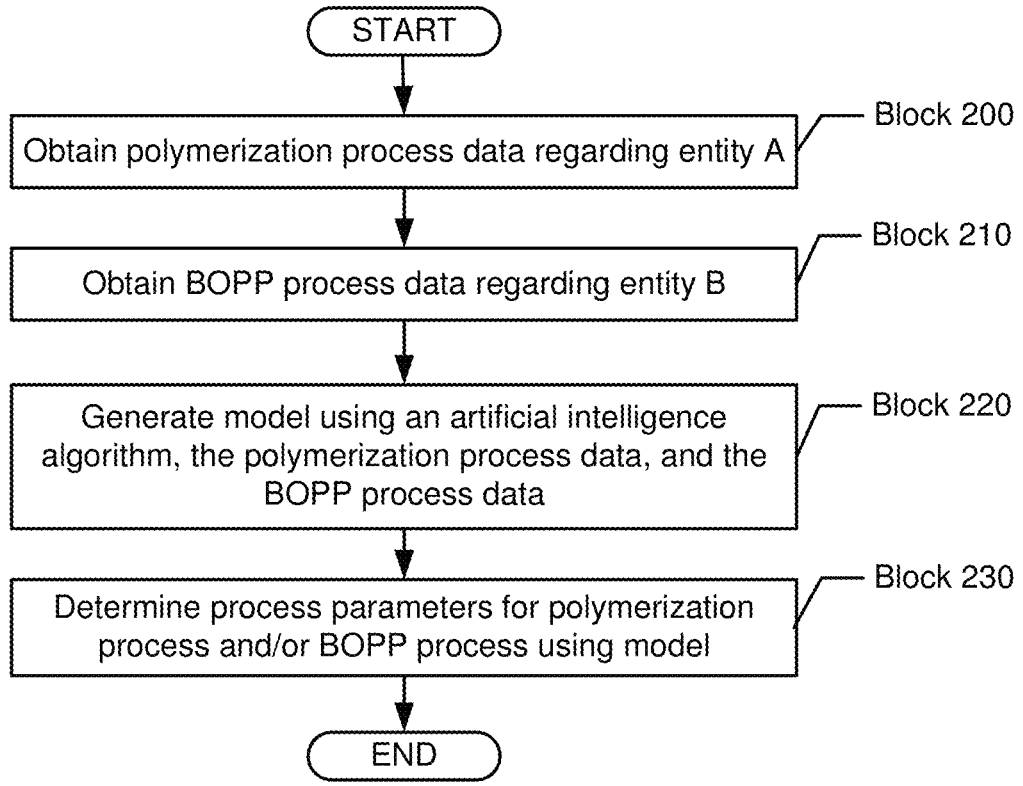
FIG. 2 shows a flowchart in accordance with one or more embodiments of the technology.

This summary is provided to introduce a selection of concepts that are further described below in the detailed description. This summary is not intended to identify key or essential features of the claimed subject matter, nor is it intended to be used as an aid in limiting the scope of the claimed subject matter.

In general, in one aspect, embodiments relate to a method that includes obtaining, by a computer processor, first data from a first entity regarding a polymerization process. The method further includes obtaining, by the computer processor, second data from a second entity regarding a production process. The method further includes generating, by the computer processor, a decision tree model using the first data, the second data, and an artificial intelligence algorithm.

In general, in one aspect, embodiments relate to a computing system that includes a processor and a memory coupled to the processor. The memory includes instructions that obtain first data from a first entity regarding a polymerization process. The memory further includes instructions that obtaining second data from a second entity regarding a production process. The memory further includes instructions that generating a decision tree model using the first data, the second data, and an artificial intelligence algorithm.

In general, in one aspect, embodiments relate to a non-transitory computer readable medium storing instructions, the instructions, when executed by a computer processor, obtain first data from a first entity regarding a polymerization process. The instructions further obtain second data from a second entity regarding a production process. The instructions further generate a decision tree model using the first data, the second data, and an artificial intelligence algorithm.

Other aspects of the disclosure will be apparent from the following description and the appended claims.

DETAILED DESCRIPTION

Specific embodiments of the technology will now be described in detail with reference to the accompanying figures. Like elements in the various figures are denoted by like reference numerals for consistency.

In the following detailed description of embodiments of the technology, numerous specific details are set forth in order to provide a more thorough understanding of the technology. However, it will be apparent to one of ordinary skill in the art that the technology may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as by the use of the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

Various embodiments are directed to a system and method to generate a model that predicts a failure rate of a final product from a polymerization process using data from multiple datasets and acquired from multiple entities. In one embodiment, for example, one dataset describes a process for producing polymers by a first entity and a different dataset that describes features from an additional polymer process from a second entity, e.g., a process to produce biaxially oriented polypropylene (BOPP) or raffia. One entity may be a resin producer, for example, while the second entity may be a customer that applies one or more additional production processes, such as compounding or forming, to the first entity's output. Using these datasets, the model may determine a probability of a product failure and identify one or more process parameters that reduce the product failure rate. For example, the system may use the model to provide a specific recommendation for multiple variables in the process for producing polypropylene and/or a recommendation of process parameters for extruding such polypropylene into a BOPP film.

In some embodiments, the model is generated using one or more artificial intelligence algorithms. For example, the artificial intelligence algorithm may use statistical correlations to create mathematical functions for classifying the success/failure rate of various process parameters. Likewise, the model may identify chemical and/or physical causes underlying product failures, as well as recommendations for different process parameters in a particular production process. In some embodiments, the model is validated periodically, e.g., to determine the stability of the model as a function of time. Validation may include scoring the model's predicted failure rate.

Turning to FIGS. 1.1-1.2, FIGS. 1.1-1.2 illustrate a system for performing a polymerization process in accordance with one or more embodiments. As shown in FIG. 1, a type of polymerization process is illustrated that uses various polymerization reactors (e.g., polymerization reactors (100)), such as loop and gas phase reactors to polymerize monomers or comonomers in the presence of a catalyst (e.g., catalyst and co-catalyst (102)), which may be optionally prepolymerized (e.g., prepolymerization stage (103)). Following polymerization/copolymerization, polymer powder is recovered, optionally additivized, and then pelletized. Each stage of the process (in particular the conditions used during process stages) may impact the chemical properties of the final resin product formed into pellets, such as, molecular weight, molecular weight distribution, stereoregularity, which may impact a melt flow rate for a given polymer grade, mechanical properties, etc. Following polymerization/copolymerization, the output is degassed, deactivated and dried. Polymer powder is collected, and then fed into an extruder where it is melted and formed into polymer pellets.

As shown in FIGS. 1.1 and 1.2, one or more components may be used in the polymerization process. Example components may include a catalyst injection pump (114), propylene (104), a hold tank (105), a reactor feed pump (106), a feedstock dryer (107), one or more pumps (108*a*, 108*b*), one or more jacket water coolers (109*a*, 109*b*), a recycle pump (110), a heater (111), a high pressure degasser (112), and/or a monomer condenser (113). Likewise, the process may also use a polymerization or copolymerization reactor (121), a degassing and deactivation step (122), and/or an extruder (123).

While FIGS. 1.1 and 1.2 show various configurations of components, other configurations may be used without departing from the scope of the disclosure. For example, various components in FIGS. 1.1 and 1.2 may be combined to create a single component. As another example, the functionality performed by a single component may be performed by two or more components.

Turning to FIG. 2, FIG. 2 shows a flowchart in accordance with one or more embodiments. Specifically, FIG. 2 describes a method for generating a model and determining process parameters from the model. While the various blocks in FIG. 2 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

In Block 200, polymerization process data is obtained regarding entity A in accordance with one or more embodiments. In some embodiments, the polymerization process data is obtained directly from a polymerization plant. For example, the polymerization process data may include sensor data that is marked with time stamps. As such, the polymerization process data may describe measurements obtained regarding one or more processes illustrated above in FIGS. 1.1 and 1.2. For example, the polymerization process data may correspond to the following processes during the production of a polymer such as a polyolefin: (1) catalytic system and pre-contact including but not limited to activation and prepolymerization; (2) first reactor polymerization; (3) second reactor polymerization; (4) degasing, deactivation and drying; (5) additivation; and (6) extrusion. For example, the polymerization process data may be categorized by polymer grade being produced so that the data collected at the polymerization to pelletization stage may be associated with the polymer grade being used for consideration in accordance with the present disclosure. In some embodiments, the polymerization process data is filtered to focus on one or more process parameters. Polymerization process data may correspond to one or more expected time intervals for a particular process for the production of polymer. Entity A may be a resin producer, producing polymer pellets for downstream use. Those skilled in the art will appreciate that entity A and entity B may be any suitable manufacturer or customer or any other entity involved in the production or use of processed polymers (e.g., pelletized product (124)).

In some embodiments, entity A and/or entity B may refer to multiple parties, e.g., entity B may include several customers using a similar process at a similar time (e.g., a network of customers with the same conversion process e.g., BOPP). Moreover, multiple polymerization entities with similar technology (e.g., Spheripol®) may learn and benefit from the same data set. Likewise, entity A can be multiple assets, as well. Thus, while FIG. 2 describes generating a model for use in connection with entity B, the model may be generated by multiple entities and/or used by multiple entities accordingly.

In some embodiments, polymerization process data corresponds to various process parameters of a polymerization process. Process parameters may include a catalyst yield, a hydrogen concentration of a reactor, a temperature of a reactor, pressure of a reactor, the polymerization output of a reactor. Other process parameters may correspond to an additivation process, such as an output of a polymer of a main feeder during additivation, an output of an additive from a feeder output during additivation, and the additive blender power during additivation. Other process parameters may include various extrusion parameters, such as pelletizer rotation speed, gear pump rotation, main engine power, die pressure, and/or temperatures in various zones of a system for performing the polymerization process.

The polymerization process data may be obtained directly from sensors. In some embodiments, the polymerization process data may include a status indicator, e.g., good or bad, of whether the sensor data was obtained on time. For example, the status indicator may identify the confidence level of the measurement of a corresponding process parameter at a given time. Thus, the polymerization process data may be filtered such that only data with a predetermined status indicator (e.g., "good") is used for further analysis. Likewise, the polymerization process data may be obtained over a computer network, e.g., a computer network (620) described in FIG. 6.2 and the accompanying description. Likewise, various quality control protocols may be performed on the polymerization process data to confirm data consistency.

In Block 210, polymer process data is obtained regarding entity B in accordance with one or more embodiments. For example, while polypropylene (or any other polymer) is produced by entity A, the downstream use of polypropylene (whether in compounding stages or forming stages) may be performed by a separate entity, such as entity B. In forming stages, a polymer is "formed" into an article, whether by extrusion, calendaring, coating, molding (including but not limited to injection molding, blow molding, etc.). In a specific example, biaxially oriented polypropylene (BOPP) is a film that is produced from a BOPP process that extrudes and stretches polymer pellets in both a machine direction orientation (MDO) and a transverse direction orientation (TDO), thus producing a molecular chain that is oriented in two directions. For example, a BOPP process may include a tubular process, in which a tubular bubble is inflated, or a tenter frame process, in which a thick extruded sheet is heated to its softening point and is mechanically stretched.

Likewise, the BOPP process data may include information regarding various BOPP products, such as mill rolls. For convenience, the present description discusses BOPP as an example for ease in explaining the present method, but the present method is not limited to polypropylene as a type of polymer or BOPP as an article formed therefrom. In some embodiments, the polymer process data is obtained from two or more entities.

Figure 3:
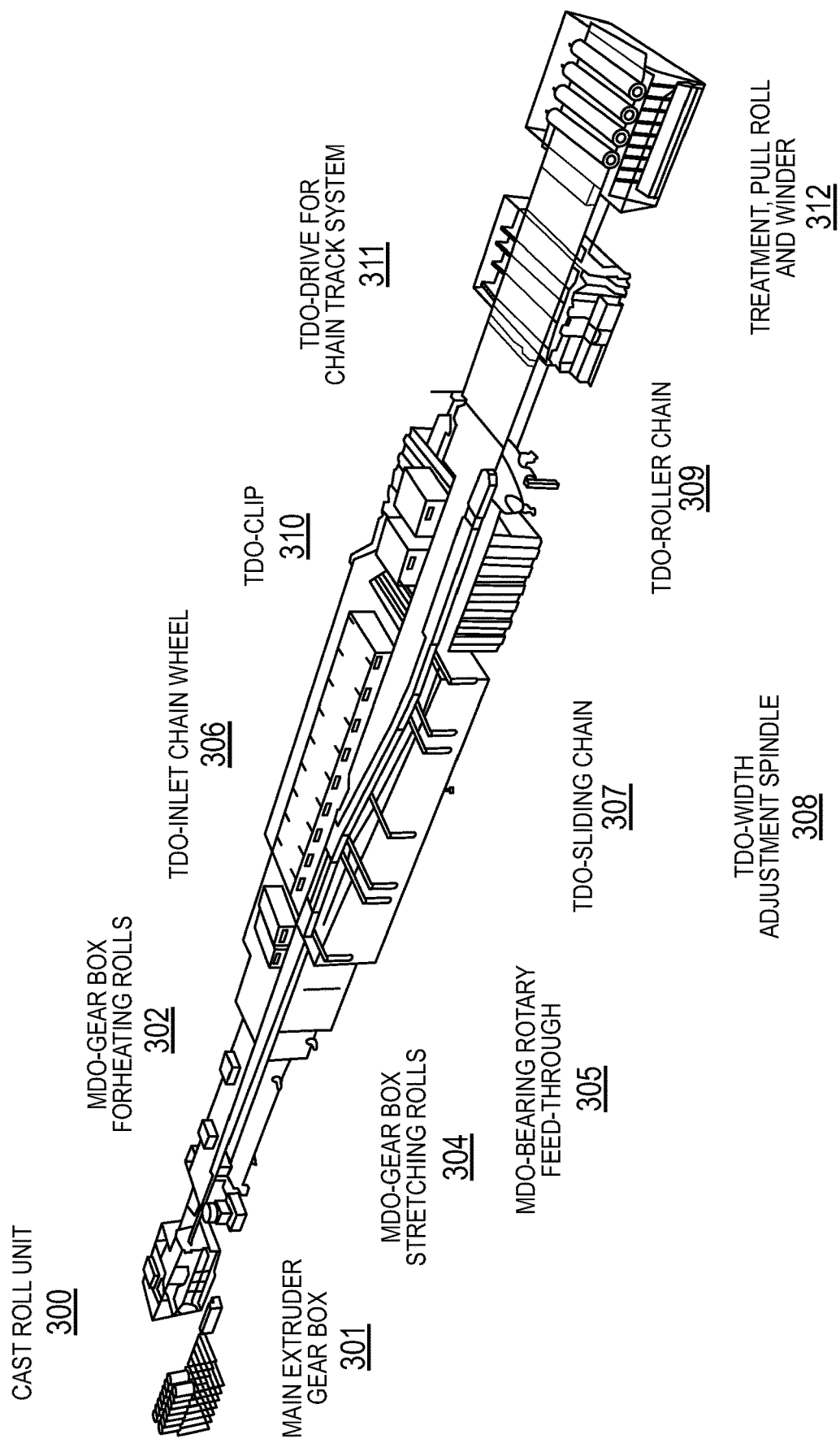

Turning to FIG. 3, FIG. 3 provides an example of a BOPP process using a cast roll unit (300). As shown in FIG. 3, various polymer pellets are transmitted through various gear boxes (e.g., main extruder gear box (301), MDO gear box for heating rolls (302)) to produce a BOPP product stretched in the machine direction orientation (MDO). Likewise, other components are shown in FIG. 3, such as a roller chain (e.g., TDO Roller Chain (309)), a width adjustment spindle (e.g., TDO width adjustment spindle (308)), gear box stretching rolls (e.g., MDO gear box stretching rolls (304)), a bearing rotary feed-through (e.g., an MDO bearing rotary feed-through (305)), a sliding chain (e.g., TDO sliding chain (307)), an inlet chain wheel (e.g., TDO inlet chain wheel (306)), a clip (e.g., TDO clip (310)), a drive for chain track system (e.g., TDO drive for chain track system), a treatment, pull roll and winder (e.g., treatment, pull roll and winder (312)), etc. to produce the BOPP product stretched in the transverse direction orientation.

Returning to FIG. 2, in some embodiments, BOPP process data corresponds to various process parameters of a BOPP process. Process parameters may include an extrusion dosing ratio, a coextrusion dosing ratio, various extrusion temperatures in various zones, a temperature of a melting pump, a melt pressure temperate at an outlet. Other process parameters may correspond to coextrusion parameters for temperatures in different zones, a melt pump temperature, a melt pressure for an outlet, and a layer thickness of a coextruder.

Moreover, process parameters may also include a chill roll MDO temperature, a casting unit annealing temperature, and a chill roll MDO speed. Process parameters of the BOPP process may further include TDO heating temperatures for different zones, winder tension values for different zones, a final roll thickness, a final role length, and a final role width. However, other process parameters are contemplated, such as for production processes for making raffia, cast films, thermoplastics, filaments, fibers, molded articles, etc.

In some embodiments, process parameters also describe the extrusion unit of the stretching machine which may be equipped with a main extruder and several coextruders in order to meet the requirements for a multilayer structure with different raw materials by means of coextrusion. One variant is the three-layer structure with one extruder for each layer. A cast roll unit may include an arrangement of a chill roll in a water bath where the velocity and temperature is controlled. The first stage of the sequential biaxial stretching process may be uniaxial in the machine direction and realized by rollers with increasing speeds and different temperature control for each step of the process, pre heating, orientation and annealing. Process parameters of the BOPP process may further include a transverse direction orientation, called TDO oven. In the transverse direction orienting machine, the MDO stretched film may be fixed with holding devices (clips) at the film edges and stretched along an adjustable rail in the transverse direction. This process may take place in an oven that is segmented into a preheating zone, a stretching zone, a thermosetting zone, and a cooling zone, and the process parameters may include heating temperatures for different zones, winder tension values for different zones, a final roll thickness, a final role length, and a final role width.

Furthermore, the BOPP process data may include information regarding operation status; sensor values in each process part of the BOPP process, e.g., for both setpoint and measurements; and final physical and statistical properties of each mill roll. The BOPP process data may also include the rankings of different process parameters by predetermined criteria, e.g., importance, during a production process. Further, BOPP process data may associate sensor measurements with a specific time in the BOPP process. In some embodiments, the BOPP process data includes information about successes and failures of the polypropylene article (film) produced from the polymerization process. For example, a BOPP process may describe one or more reasons why each BOPP product, e.g., a mill roll, was rejected as a failure. In some embodiments, a failure of the BOPP product is associated with a specific cause of the failure, e.g., oil supply parameters, main extrusion filter heating parameters, TDO cooling fan parameters, TDO heating fans outlet parameters, and/or winder pressure and tension parameters.

Figure 4:
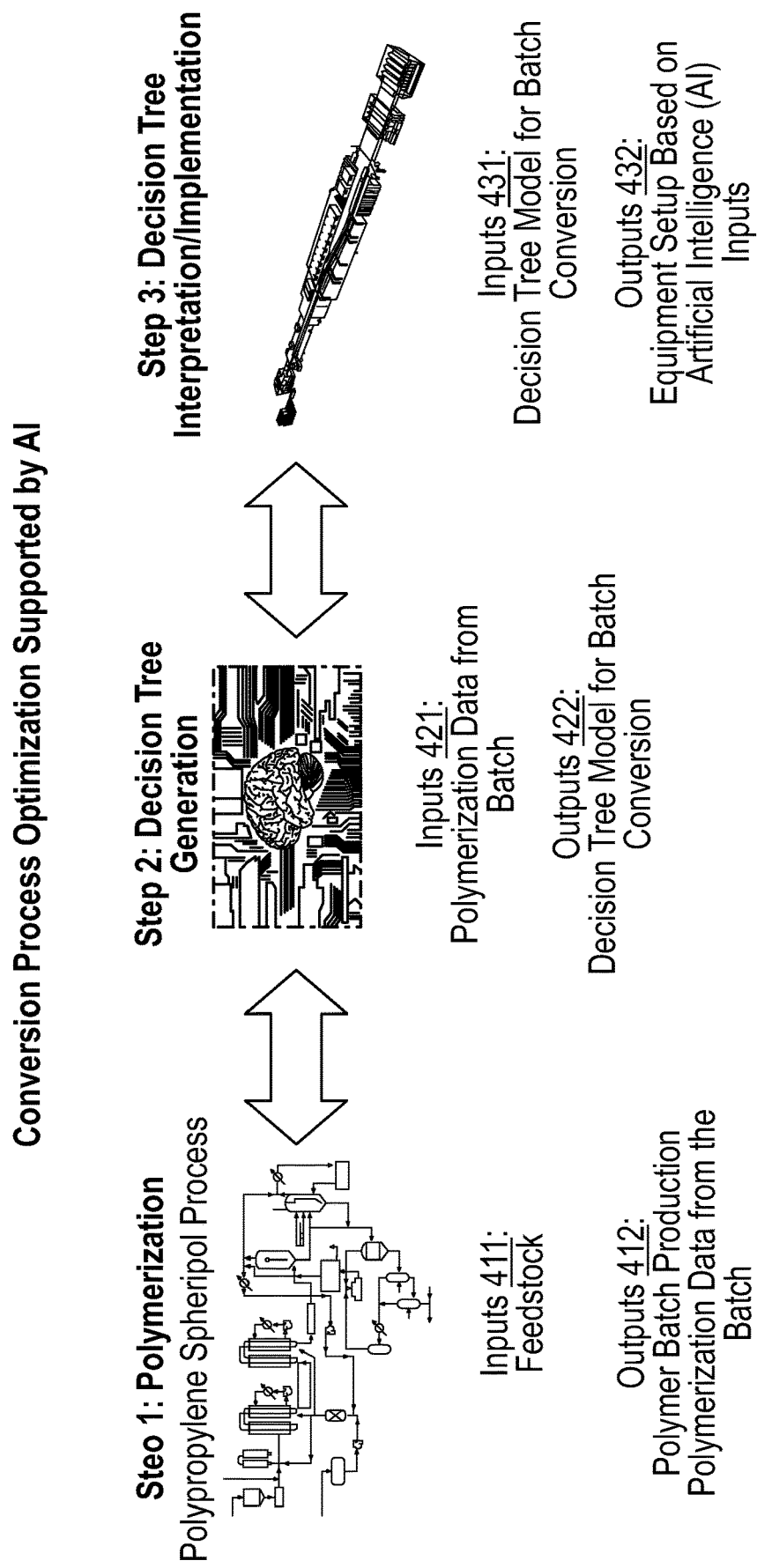

In Block 220, a model is generated using an artificial intelligence algorithm, polymerization process data, and BOPP process data in accordance with one or more embodiments. That is, the polymerization process data and BOPP process data are inputs into the AI algorithm, which then processes the data by cleaning up the data to include only the relevant information and produces an output using AI business rule logic and algorithms. For example, the artificial intelligence algorithm may be a machine learning algorithm, where portions of the polymerization process data and the BOPP process data are provided as input characteristics to the machine learning algorithm. Likewise, data may be preconditioned as inputs for the artificial intelligence algorithm, e.g., by determining mean values, standard deviations, maximums, minimums, skewness, kurtosis, and 5-momentum correlation function and outliers, such as per sensor. In some embodiments, outlier values are identified either as part of the artificial intelligence algorithm or prior to use as inputs to the artificial intelligence algorithm. Likewise, the polymerization process data and the BOPP process data may be aggregated into a joint data set in order to generate the model. FIG. 4 show an example of using polymerization process data and BOPP process data to generate a model. As shown in FIG. 4, for example, Step 1 may be a polymerization process, Step 2 may be a decision tree generation process, and Step 3 may be an implementation of a decision tree. In Step 1, the inputs (411) may be feedstock, while the outputs (412) may be polymer batch production polymerization data from a batch. In Step 2, the inputs (421) may be the polymerization data from a batch and the outputs (422) may be a decision tree model for batch conversion. In Step 3, the inputs (431) may be a decision tree model for batch conversion, while the outputs (432) may be equipment set up based on artificial intelligence inputs.

In some embodiments, the model is a machine-learning model. For example, different types of machine-learning models may be generated, such as convolutional neural networks, deep neural networks, recurrent neural networks, support vector machines, decision tree models, inductive learning models, deductive learning models, supervised learning models, etc. In some embodiments, a machine-learning model is trained using augmented or synthetic data (in addition to or in place of acquired data) to produce a large amount of interpreted data for training a particular model. In some embodiments, the model is a random forest classifier model that includes multiple decision tree. A random forest classifier model may be trained using a supervised learning algorithm, for example.

In some embodiments, a model is trained using multiple machine-learning epochs. For example, a machine-learning epoch may be an iteration of a model through a portion or all of the training dataset. For example, a single machine-learning epoch may correspond to a specific batch of polymerization data or production process data, where the training dataset is divided into multiple batches for multiple epochs. Thus, a model may be trained iteratively using epochs until the model achieves a predetermined level of accuracy in predicting a polymerization process or a production process. In some embodiments, a certain percentage of acquired data and augmented data may be imported into a particular epoch to strengthen the training part of the machine-learning algorithm. Better training of the model which in turn may lead to better predictions for updating the model. Once the training dataset is passed through all of the epochs and the model is further updated based on the model's predictions in each epoch, a trained model may be the final result of the machine-learning algorithm. In some embodiments, multiple trained models are compared and the best trained model is selected accordingly.

In some embodiments, the model classifies one or more polymerization process inputs and/or production process inputs to one or more identified classes (e.g., end nodes in a decision tree). This classification may be a binary classification with two possible labels, or a multi-classification output. For more information on machine-learning classifications, see the description regarding a classification system below.

Keeping with Block 220, the model may be generated by identifying correlations within the joint data set and thus determining causal reasons that describe successes and failures in BOPP production process. In some embodiments, clustering techniques are applied to the BOPP process data. For example, the clustering techniques may include the following: K-Means using an elbow method to determine the cluster numbers; K-Means using a silhouette coefficient; and K-Medians using Principal Component Analysis and using 2 variables for visualization. By using the BOPP data with a cluster, clustering variables may be identified. However, when features from the polymerization process data are used on the joint dataset, clustering variables from the BOPP process data may no longer be identifiable.

In some embodiments, the model is generated using a classification system to produce a decision tree model. In a decision tree model, grouping may be used to reduce the number of similar variables within the decision tree in order to classify process parameters that produce failures and successes. A decision tree model may generate interdependent and sequential cuts in the various input variables to produce a prediction of a particular class as a response (e.g., "optimal" or "not-optimal", "failure", "success"). The predetermined criterion used to create the sequential cuts may be the minimization of measures of impurity or entropy in the data used for training the model.

Turning to FIGS. 5.1 and 5.2, FIGS. 5.1 and 5.2 provide examples of decision trees with corresponding process parameters. For example, a decision tree model may include chance nodes, decision nodes, and end nodes. A chance node may identify a probability of a particular result or outcome. A decision node may correspond to a decision that is made within a decision tree (e.g., decision nodes (501, 502, 503, 506, 507, 508, 509, 510, 513) in FIG. 5.1 or decision nodes (520, 521, 523, 525, 526, 529, 530, 532) in FIG. 5.2). An end node may show the final outcome of a decision path (e.g., end nodes (504, 505, 511, 512, 514, 515, 516, 517, 518, 519) or end nodes (522, 524, 527, 528, 531, 533, 534, 535, 536)). As such, decision tree nodes may be arranged according to multiple decision levels. Furthermore, branches in a decision tree model may include a set of attributes or classification rules. These classification rules (also called decision rules) may result in a particular class label that is found in a corresponding end node at the end of the branch. Classification rules may be expressed in an if-then clause, with each decision or data value forming a clause, such that, if a specific condition or conditions are fulfilled, then a specific outcome will result with a particular amount of certainty.

In some embodiments, a decision-tree generation algorithm builds and/or trains a decision tree model from the top decision-tree nodes downward by selecting a variable at each generation step that best divides a set of items. For example, different decision-tree generation algorithms may use different metrics for determining a "best" variable or "best" variables at a particle decision node. Example metrics include Gini impurity values, information gain, and variance reductions. In FIGS. 5.1 and 5.2, for example, each decision-tree node includes a Gini Impurity value (e.g., "gini=0.275" or "gini=0.244"). Gini Impurity may a measure of how often a randomly selected element would be incorrectly classified if it was randomly classified according to a particular class distribution in a databset. In other words, a Gini Impurity value may correspond to a probability that a datapoint is classified correctly. For example, a Gini Impurity value of '0' may the lowest possible value as well as the best impurity value. A Gini Impurity value of '0' may only be achieved when each element is the same class in an element distribution. When training a decision tree model, the best split may be selected by maximizing the Gini gain value. More specifically, a Gini gain value may be calculated by subtracting various weighted impurities of the branches from the original impurity. A higher Gini gain value corresponds to a better split.

Keeping with a decision tree (DT) model, a decision tree model may include a computer that receives a training table where the last column contains the class to which the product belongs ("failed" or "success"), where this column with the known class is known as the label column in machine learning literature. For example, the training table that goes into generating the model may have one BOPP product per row and each column represents values of those BOPP products, with the last column may be a value of 1 or 0. The artificial intelligence algorithm may identify correlations in the joint data set to predict, given a new row of an assembly not used for training and without the last label column, whether the BOPP product will be 0 or 1 (i.e., a success or failure).

In some embodiments, the model is trained using a train-test split, i.e., by dividing data into training dataset and testing dataset. For example, the model may be trained using a random split 70% and 30% of the joint dataset to train and test the model, respectively. For example, using clusters of the BOPP process data and generate a model that includes multiple decision trees. For example, the model may be a random forest model. In a random forest model, the features from the data with the most importance correspond to the Random Forest Classifier. These features may be hyperparameters among the process parameters for use in a decision tree, and the hyperparameters may be determined from the following: process parameters that have more observations and confidence in their prediction, such as parameters that balance class weight; feature parameters from the polymerization process, etc.

In some embodiments, a cumulative window is used to generate the model. For example, the polymerization process data and/or the BOPP process data may be trained cumulatively. For example, a sample dataset of BOPP products is acquired to train and validate the model. After analyzing a predetermined number of BOPP product successes and failures, a following number of successes/failures may be predicted. Thus, a complete dataset may be trained iteratively. Using a train-test split configuration, one or more of the following techniques may be used: selecting features from a Random Forest model; a synthetic minority over-sampling technique (SMOTE) to obtain a best-balanced failures and success distribution; a resampling technique; a minimum samples leaf technique; and a minimum threshold technique that accepts a predetermined number, e.g., equals 90%.

In some embodiments, a model is generated using one or more moving windows. For example, data may be trained using different periods for analysis, such as without accumulating data on the training dataset. For example, the last 150 BOPP products may be used to predict the next 24 BOPP products. Applying this technique with time intervals, multiple decision trees are produced using a joint data set.

In Block 230, various process parameters are determined for a polymerization process and/or a BOPP process using a model in accordance with one or more embodiments. For example, some process parameters in the polymerization process may behave according to a substantially gaussian distribution. However, process parameters may include various peaks and a non-gaussian structure. Thus, a model may determine which process parameters of the polymerization process and/or the BOPP process can be adjusted in order to reduce or eliminate failures in the BOPP process.

In some embodiments, a recommendation is transmitted to an entity in response to various input parameters and design specifications. For example, given a particular BOPP production process, a user device may transmit process parameter values to a server that can access a model similar to the model generated in Block 220. For example, the user device may provide a user interface where a user selects one or more process parameters for optimization, e.g., a humans may filter or choose variables to feed an artificial intelligence algorithm to prioritize or emphasize certain process parameters. User selection may also be an input to generating the model, by evaluating and improving correlation between various user priorities and the model's output. For a decision tree model, user selection inputs may be used to eliminate certain nodes/branches as well as identify correlations that do not make sense or have less importance in the production process.

Further, the server may then optimize the process parameters in the polymerization process and/or recommend changes to process parameters in the BOPP process. In some embodiments, process parameter values are obtained automatically from one or more entities, e.g., through network communication between remote servers coupled to different production plants. Thus, optimization for a production process and/or a polymerization process may be performed in some embodiments without human intervention. Likewise, given a particular set of process parameters for a BOPP process, a message may be generated that identifies a predicted failure rate of a polymer pellet during the BOPP process. Thus, a user device may communicate with the model to optimize the polymerization process to reduce the failure rate of the BOPP products.

In some embodiments, the model generated in FIG. 2 provides recommendations for a production process. For example, the model may determine one or more process parameters for an existing pellet in order for the existing pellet to perform better in a target production process application. Likewise, embodiments may also optimize process parameters in a production process.

While FIG. 2 describes many embodiments relating to a BOPP process, other production process are contemplated for model generation using other polymerization processes. For example, a model may be generated using process data for producing raffia, cast films, molded articles, filaments, fibers, thermoforming, etc.

Embodiments may be implemented on a computing system. Any combination of mobile, desktop, server, router, switch, embedded device, or other types of hardware may be used. For example, as shown in FIG. 6.1, the computing system (600) may include one or more computer processors (602), non-persistent storage (604) (e.g., volatile memory, such as random access memory (RAM), cache memory), persistent storage (606) (e.g., a hard disk, an optical drive such as a compact disk (CD) drive or digital versatile disk (DVD) drive, a flash memory, etc.), a communication interface (612) (e.g., Bluetooth interface, infrared interface, network interface, optical interface, etc.), and numerous other elements and functionalities.

The computer processor(s) (602) may be an integrated circuit for processing instructions. For example, the computer processor(s) may be one or more cores or micro-cores of a processor. The computing system (600) may also include one or more input devices (610), such as a touchscreen, keyboard, mouse, microphone, touchpad, electronic pen, or any other type of input device.

The communication interface (612) may include an integrated circuit for connecting the computing system (600) to a network (not shown) (e.g., a local area network (LAN), a wide area network (WAN) such as the Internet, mobile network, or any other type of network) and/or to another device, such as another computing device.

Further, the computing system (600) may include one or more output devices (608), such as a screen (e.g., a liquid crystal display (LCD), a plasma display, touchscreen, cathode ray tube (CRT) monitor, projector, or other display device), a printer, external storage, or any other output device. One or more of the output devices may be the same or different from the input device(s). The input and output device(s) may be locally or remotely connected to the computer processor(s) (602), non-persistent storage (604), and persistent storage (606). Many different types of computing systems exist, and the aforementioned input and output device(s) may take other forms.

Software instructions in the form of computer readable program code to perform embodiments of the disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), is configured to perform one or more embodiments of the disclosure.

The computing system (600) in FIG. 6.1 may be connected to or be a part of a network. For example, as shown in FIG. 6.2, the network (620) may include multiple nodes (e.g., node X (622), node Y (624)). Each node may correspond to a computing system, such as the computing system shown in FIG. 6.1, or a group of nodes combined may correspond to the computing system shown in FIG. 6.1. By way of an example, embodiments of the disclosure may be implemented on a node of a distributed system that is connected to other nodes. By way of another example, embodiments of the disclosure may be implemented on a distributed computing system having multiple nodes, where each portion of the disclosure may be located on a different node within the distributed computing system. Further, one or more elements of the aforementioned computing system (600) may be located at a remote location and connected to the other elements over a network.

Although not shown in FIG. 6.2, the node may correspond to a blade in a server chassis that is connected to other nodes via a backplane. By way of another example, the node may correspond to a server in a data center. By way of another example, the node may correspond to a computer processor or micro-core of a computer processor with shared memory and/or resources.

The nodes (e.g., node X (622), node Y (624)) in the network (620) may be configured to provide services for a client device (626). For example, the nodes may be part of a cloud computing system. The nodes may include functionality to receive requests from the client device (626) and transmit responses to the client device (626). The client device (626) may be a computing system, such as the computing system shown in FIG. 6.1. Further, the client device (626) may include and/or perform all or a portion of one or more embodiments of the disclosure.

The computing system or group of computing systems described in FIGS. 6.1 and 6.2 may include functionality to perform a variety of operations disclosed herein. For example, the computing system(s) may perform communication between processes on the same or different systems. A variety of mechanisms, employing some form of active or passive communication, may facilitate the exchange of data between processes on the same device. Examples representative of these inter-process communications include, but are not limited to, the implementation of a file, a signal, a socket, a message queue, a pipeline, a semaphore, shared memory, message passing, and a memory-mapped file. Further details pertaining to a couple of these non-limiting examples are provided below.

Based on the client-server networking model, sockets may serve as interfaces or communication channel endpoints enabling bidirectional data transfer between processes on the same device. Foremost, following the client-server networking model, a server process (e.g., a process that provides data) may create a first socket object. Next, the server process binds the first socket object, thereby associating the first socket object with a unique name and/or address. After creating and binding the first socket object, the server process then waits and listens for incoming connection requests from one or more client processes (e.g., processes that seek data). At this point, when a client process wishes to obtain data from a server process, the client process starts by creating a second socket object. The client process then proceeds to generate a connection request that includes at least the second socket object and the unique name and/or address associated with the first socket object. The client process then transmits the connection request to the server process. Depending on availability, the server process may accept the connection request, establishing a communication channel with the client process, or the server process, busy in handling other operations, may queue the connection request in a buffer until the server process is ready. An established connection informs the client process that communications may commence. In response, the client process may generate a data request specifying the data that the client process wishes to obtain. The data request is subsequently transmitted to the server process. Upon receiving the data request, the server process analyzes the request and gathers the requested data. Finally, the server process then generates a reply including at least the requested data and transmits the reply to the client process. The data may be transferred, more commonly, as datagrams or a stream of characters (e.g., bytes).

Shared memory refers to the allocation of virtual memory space in order to substantiate a mechanism for which data may be communicated and/or accessed by multiple processes. In implementing shared memory, an initializing process first creates a shareable segment in persistent or non-persistent storage. Post creation, the initializing process then mounts the shareable segment, subsequently mapping the shareable segment into the address space associated with the initializing process. Following the mounting, the initializing process proceeds to identify and grant access permission to one or more authorized processes that may also write and read data to and from the shareable segment. Changes made to the data in the shareable segment by one process may immediately affect other processes, which are also linked to the shareable segment. Further, when one of the authorized processes accesses the shareable segment, the shareable segment maps to the address space of that authorized process. Often, one authorized process may mount the shareable segment, other than the initializing process, at any given time.

Other techniques may be used to share data, such as the various data described in the present application, between processes without departing from the scope of the disclosure. The processes may be part of the same or different application and may execute on the same or different computing system.

Rather than or in addition to sharing data between processes, the computing system performing one or more embodiments of the disclosure may include functionality to receive data from a user. For example, in one or more embodiments, a user may submit data via a graphical user interface (GUI) on the user device. Data may be submitted via the graphical user interface by a user selecting one or more graphical user interface widgets or inserting text and other data into graphical user interface widgets using a touchpad, a keyboard, a mouse, or any other input device. In response to selecting a particular item, information regarding the particular item may be obtained from persistent or non-persistent storage by the computer processor. Upon selection of the item by the user, the contents of the obtained data regarding the particular item may be displayed on the user device in response to the user's selection.

By way of another example, a request to obtain data regarding the particular item may be sent to a server operatively connected to the user device through a network. For example, the user may select a uniform resource locator (URL) link within a web client of the user device, thereby initiating a Hypertext Transfer Protocol (HTTP) or other protocol request being sent to the network host associated with the URL. In response to the request, the server may extract the data regarding the particular selected item and send the data to the device that initiated the request. Once the user device has received the data regarding the particular item, the contents of the received data regarding the particular item may be displayed on the user device in response to the user's selection. Further to the above example, the data received from the server after selecting the URL link may provide a web page in Hyper Text Markup Language (HTML) that may be rendered by the web client and displayed on the user device.

Once data is obtained, such as by using techniques described above or from storage, the computing system, in performing one or more embodiments of the disclosure, may extract one or more data items from the obtained data. For example, the extraction may be performed as follows by the computing system (600) in FIG. 6.1. First, the organizing pattern (e.g., grammar, schema, layout) of the data is determined, which may be based on one or more of the following: position (e.g., bit or column position, Nth token in a data stream, etc.), attribute (where the attribute is associated with one or more values), or a hierarchical/tree structure (consisting of layers of nodes at different levels of detail—such as in nested packet headers or nested document sections). Then, the raw, unprocessed stream of data symbols is parsed, in the context of the organizing pattern, into a stream (or layered structure) of tokens (where each token may have an associated token "type").

Next, extraction criteria are used to extract one or more data items from the token stream or structure, where the extraction criteria are processed according to the organizing pattern to extract one or more tokens (or nodes from a layered structure). For position-based data, the token(s) at the position(s) identified by the extraction criteria are extracted. For attribute/value-based data, the token(s) and/or node(s) associated with the attribute(s) satisfying the extraction criteria are extracted. For hierarchical/layered data, the token(s) associated with the node(s) matching the extraction criteria are extracted. The extraction criteria may be as simple as an identifier string or may be a query presented to a structured data repository (where the data repository may be organized according to a database schema or data format, such as XML).

The extracted data may be used for further processing by the computing system. For example, the computing system of FIG. 6.1, while performing one or more embodiments of the disclosure, may perform data comparison. Data comparison may be used to compare two or more data values (e.g., A, B). For example, one or more embodiments may determine whether A>B, A=B, A !=B, A<B, etc. The comparison may be performed by submitting A, B, and an opcode specifying an operation related to the comparison into an arithmetic logic unit (ALU) (i.e., circuitry that performs arithmetic and/or bitwise logical operations on the two data values). The ALU outputs the numerical result of the operation and/or one or more status flags related to the numerical result. For example, the status flags may indicate whether the numerical result is a positive number, a negative number, zero, etc. By selecting the proper opcode and then reading the numerical results and/or status flags, the comparison may be executed. For example, in order to determine if A>B, B may be subtracted from A (i.e., A−B), and the status flags may be read to determine if the result is positive (i.e., if A>B, then A−B>0). In one or more embodiments, B may be considered a threshold, and A is deemed to satisfy the threshold if A=B or if A>B, as determined using the ALU. In one or more embodiments of the disclosure, A and B may be vectors, and comparing A with B includes comparing the first element of vector A with the first element of vector B, the second element of vector A with the second element of vector B, etc. In one or more embodiments, if A and B are strings, the binary values of the strings may be compared.

The computing system in FIG. 6.1 may implement and/or be connected to a data repository. For example, one type of data repository is a database. A database is a collection of information configured for ease of data retrieval, modification, re-organization, and deletion. Database Management System (DBMS) is a software application that provides an interface for users to define, create, query, update, or administer databases.

The user, or software application, may submit a statement or query into the DBMS. Then the DBMS interprets the statement. The statement may be a select statement to request information, update statement, create statement, delete statement, etc. Moreover, the statement may include parameters that specify data, or data container (database, table, record, column, view, etc.), identifier(s), conditions (comparison operators), functions (e.g. join, full join, count, average, etc.), sort (e.g. ascending, descending), or others. The DBMS may execute the statement. For example, the DBMS may access a memory buffer, a reference or index a file for read, write, deletion, or any combination thereof, for responding to the statement. The DBMS may load the data from persistent or non-persistent storage and perform computations to respond to the query. The DBMS may return the result(s) to the user or software application.

The computing system of FIG. 6.1 may include functionality to present raw and/or processed data, such as results of comparisons and other processing. For example, presenting data may be accomplished through various presenting methods. Specifically, data may be presented through a user interface provided by a computing device. The user interface may include a GUI that displays information on a display device, such as a computer monitor or a touchscreen on a handheld computer device. The GUI may include various GUI widgets that organize what data is shown as well as how data is presented to a user. Furthermore, the GUI may present data directly to the user, e.g., data presented as actual data values through text, or rendered by the computing device into a visual representation of the data, such as through visualizing a data model.

For example, a GUI may first obtain a notification from a software application requesting that a particular data object be presented within the GUI. Next, the GUI may determine a data object type associated with the particular data object, e.g., by obtaining data from a data attribute within the data object that identifies the data object type. Then, the GUI may determine any rules designated for displaying that data object type, e.g., rules specified by a software framework for a data object class or according to any local parameters defined by the GUI for presenting that data object type. Finally, the GUI may obtain data values from the particular data object and render a visual representation of the data values within a display device according to the designated rules for that data object type.

Data may also be presented through various audio methods. In particular, data may be rendered into an audio format and presented as sound through one or more speakers operably connected to a computing device.

Data may also be presented to a user through haptic methods. For example, haptic methods may include vibrations or other physical signals generated by the computing system. For example, data may be presented to a user using a vibration generated by a handheld computer device with a predefined duration and intensity of the vibration to communicate the data.

The above description of functions presents only a few examples of functions performed by the computing system of FIG. 6.1 and the nodes and/or client device in FIG. 6.2.

Other functions may be performed using one or more embodiments of the disclosure.

While the technology has been described with respect to a limited number of embodiments, those skilled in the art, having benefit of this disclosure, will appreciate that other embodiments can be devised which do not depart from the scope of the technology as disclosed herein. Accordingly, the scope of the technology should be limited only by the attached claims.

What is claimed is:

1. A method, comprising:
   obtaining, by a computer processor, first polymerization data from a first entity regarding a polymerization process using a first plurality of sensors and at least one polymerization reactor, wherein the first polymerization data comprises sensor data regarding a reactor polymerization using the at least one polymerization reactor;
   obtaining, by the computer processor, first process data from a second entity regarding a polypropylene production process for a plurality of polypropylene products using a second plurality of sensors,
   wherein the first polymerization data and the first process data are obtained over a computer network;
   generating, by the computer processor, a decision tree model using the first polymerization data, the first process data, and an artificial intelligence algorithm,
   wherein the decision tree model models one or more chemical properties or one or more mechanical properties of a polypropylene article that is produced from the polymerization process and the polypropylene production process;
   obtaining, from a user device and using a user interface, a user selection of a selected process parameter for a biaxially oriented polypropylene (BOPP) process;
   obtaining, from a first temperature sensor connected to a polymerization reactor, a first temperature sensor value of the polymerization reactor for the polymerization process;
   obtaining, from a second temperature sensor, a second temperature sensor value that corresponds to an extrusion temperature of an extruder that is used in the polypropylene production process;
   determining, by the computer processor, a first polymerization process parameter value for the polymerization process and a BOPP production process parameter value for the BOPP process based on the user selection of the selected process parameter, the first temperature sensor value of the polymerization process, and the second temperature sensor value as inputs to the decision tree model;
   performing the polymerization process using the polymerization reactor and based on the first temperature sensor value and the first polymerization process parameter value to produce a plurality of polymers; and
   producing a BOPP film using the plurality of polymers and the BOPP process comprising the extruder and based on the second temperature sensor value and the BOPP production process parameter value, and
   wherein the BOPP production process parameter value describes an operation of the extruder.

2. The method of claim 1,
   wherein the artificial intelligence algorithm is a machine-learning algorithm,
   wherein generating the decision tree model comprises training the decision tree model using a training dataset and a testing dataset,
   wherein the training dataset comprises a first batch of polymerization data or a first batch of production process data, and
   wherein the testing dataset comprises a second batch of polymerization data or a second batch of production process data that is separate from data used in the training dataset.

3. The method of claim 1,
   wherein the decision tree model is a random forest classifier model,
   wherein the artificial intelligence algorithm is a supervised learning algorithm, and
   wherein the random forest classifier model comprises a plurality of end nodes corresponding to different labeled classes.

4. The method of claim 1, further comprising:
   determining one or more process parameters for optimizing one or more steps in the polymerization process using the decision tree model.

5. The method of claim 1, further comprising:
   determining one or more process parameters for optimizing one or more steps in the polypropylene production process using the decision tree model.

6. A system, comprising:
   a polymerization reactor connected to a first temperature sensor;
   an extruder connected to a second temperature sensor;
   a computer network connected to the first temperature sensor and the second temperature sensor;
   a first plurality of sensors connected to the computer network;
   a second plurality of sensors connected to the computer network;
   a user device connected to the computer network, the user device being configured to provide a user interface; and
   a computer system comprising a processor, and a memory coupled to the processor,
   wherein the computer system, the first plurality of sensors, the second plurality of sensors, the first temperature sensor, the second temperature sensor, and the user device are connected over the computer network, and
   wherein the user device obtains a user selection of a selected process parameter for a biaxially oriented polypropylene (BOPP) process,
   wherein the memory comprises instructions with functionality for:
      obtaining first polymerization data from a first entity regarding a polymerization process using the first plurality of sensors and at least one polymerization reactor, wherein the first polymerization data comprises sensor data regarding a reactor polymerization using the at least one polymerization reactor;
      obtaining first process data from a second entity regarding a polypropylene production process for a plurality of polypropylene products using the second plurality of sensors,
      wherein the first polymerization data and the first process data are obtained over the computer network, and
      generating a decision tree model using the first polymerization data, the first process data, and an artificial intelligence algorithm,
      wherein the decision tree model models one or more chemical properties or one or more mechanical properties of a polypropylene article that is produced from the polymerization process and the polypropylene production process, obtaining, from the first temperature sensor, a first temperature sensor value of the polymerization reactor for the polymerization process;

obtaining, from the second temperature sensor, a second temperature sensor value that corresponds to an extrusion temperature of the extruder that is used in the polypropylene production process;

determining a first polymerization process parameter value for the polymerization process and a BOPP production process parameter value for the BOPP process based on the user selection of the selected process parameter, the first temperature sensor value of the polymerization process, and the second temperature sensor value as inputs to the decision tree model;

performing the polymerization process using the polymerization reactor and based on the first temperature sensor value and the first polymerization process parameter value to produce a plurality of polymers; and producing a BOPP film using the plurality of polymers and the BOPP process comprising the extruder and based on the second temperature sensor value and the BOPP production process parameter value, and wherein the BOPP production process parameter value describes an operation of the extruder.

7. The system of claim 6,
wherein the artificial intelligence algorithm is a machine-learning algorithm,
wherein generating the decision tree model comprises training the decision tree model using a training dataset and a testing dataset,
wherein the training dataset comprises a first batch of polymerization data or a first batch of production process data, and
wherein the testing dataset comprises a second batch of polymerization data or a second batch of production process data that is separate from data used in the training dataset.

8. The system of claim 6, wherein the memory further comprises instructions with functionality for:
determining one or more process parameters for optimizing one or more steps in the polymerization process using the decision tree model.

9. The system of claim 6, wherein the memory further comprises instructions with functionality for:
determining one or more process parameters for optimizing one or more steps in the polypropylene production process using the decision tree model.

10. The system of claim 6,
wherein the decision tree model is a random forest classifier model,
wherein the artificial intelligence algorithm is a supervised learning algorithm, and
wherein the random forest classifier model comprises a plurality of end nodes corresponding to different labeled classes.

11. A non-transitory computer readable medium storing instructions, the instructions, when executed by a computer processor, comprising functionality for:
obtaining first polymerization data from a first entity regarding a polymerization process using a first plurality of sensors and at least one polymerization reactor,
wherein the first polymerization data comprises sensor data regarding a reactor polymerization using the at least one polymerization reactor;

obtaining first process data from a second entity regarding a polypropylene production process for a plurality of polypropylene products using a second plurality of sensors,
wherein the first polymerization data and the first process data are obtained over a computer network;
generating a decision tree model using the first polymerization data, the first process data, and an artificial intelligence algorithm,
wherein the decision tree model models one or more chemical properties or one or more mechanical properties of a polypropylene article that is produced from the polymerization process and the polypropylene production process;
obtaining, from a user device and using a user interface, a user selection of a selected process parameter for a biaxially oriented polypropylene (BOPP) process;
obtaining, from a first temperature sensor connected to a polymerization reactor, a first temperature sensor value of the polymerization reactor for the polymerization process;
obtaining, from a second temperature sensor, a second temperature sensor value that corresponds to an extrusion temperature of an extruder that is used in the polypropylene production process;
determining a first polymerization process parameter value for the polymerization process and a BOPP production process parameter value for the BOPP process based on the user selection of the selected process parameter, the first temperature sensor value of the polymerization process, and the second temperature sensor value as inputs to the decision tree model;
performing the polymerization process using the polymerization reactor and based on the first temperature sensor value and the first polymerization process parameter value to produce a plurality of polymers; and
producing a BOPP film using the plurality of polymers and the BOPP process comprising the extruder and based on the second temperature sensor value and the BOPP production process parameter value, and
wherein the BOPP production process parameter value describes an operation of the extruder.

12. The non-transitory computer readable medium of claim 11,
wherein the artificial intelligence algorithm is a machine-learning algorithm,
wherein generating the decision tree model comprises training the decision tree model using a training dataset and a testing dataset,
wherein the training dataset comprises a first batch of polymerization data or a first batch of production process data, and
wherein the testing dataset comprises a second batch of polymerization data or a second batch of production process data that is separate from data used in the training dataset.

13. The non-transitory computer readable medium of claim 11, wherein the instructions further comprise functionality for:
determining one or more process parameters for optimizing one or more steps in the polymerization process using the decision tree model.

14. The non-transitory computer readable medium of claim 11, wherein the instructions further comprise functionality for:

determining one or more process parameters for optimizing one or more steps in the polypropylene production process using the decision tree model.

15. The non-transitory computer readable medium of claim 11,
wherein the decision tree model is a random forest classifier model,
wherein the artificial intelligence algorithm is a supervised learning algorithm, and
wherein the random forest classifier model comprises a plurality of end nodes corresponding to different labeled classes.

16. The method of claim 1,
wherein the BOPP production process parameter value is selected from a group consisting of a transverse direction orientation (TDO) heating temperature, a winder tension value, and a roll thickness.

* * * * *